(12) United States Patent
Hutchinson

(10) Patent No.: US 6,524,264 B1
(45) Date of Patent: Feb. 25, 2003

(54) FRONT AND BACK BRACE WITH CONTACT SEPARATION COVER

(76) Inventor: Ethel Hutchinson, 2821 Hobson Rd. (Unit 2), Woodridge, IL (US) 60517

( * ) Notice: Subject to any disclaimer, the term of this patent is extended or adjusted under 35 U.S.C. 154(b) by 69 days.

(21) Appl. No.: 09/679,218

(22) Filed: Oct. 5, 2000

(51) Int. Cl.[7] ............... A61F 5/00; A61F 5/24
(52) U.S. Cl. .................. 602/19; 128/96.1
(58) Field of Search .......... 602/4–5, 12, 18–19, 602/60–65, 75–76; 128/876, DIG. 23, 96.1; 2/311, 312, 338, 44, 22

(56) References Cited

U.S. PATENT DOCUMENTS

| | | | | |
|---|---|---|---|---|
| 2,811,154 A | * | 10/1957 | Scholl | 602/75 |
| 3,921,626 A | * | 11/1975 | Neel | 602/18 |
| 5,010,877 A | * | 4/1991 | Druskoczi | 602/18 |
| 5,267,948 A | * | 12/1993 | Elliott | 602/19 |
| 5,425,702 A | * | 6/1995 | Carn | 602/62 |
| 5,433,697 A | * | 7/1995 | Cox | 602/19 |
| D365,398 S | * | 12/1995 | Maynard | |
| 5,538,500 A | * | 7/1996 | Peterson | 602/48 |
| 5,598,583 A | * | 2/1997 | Victor | 2/46 |
| 5,628,063 A | * | 5/1997 | Reed | 2/22 |
| 5,722,939 A | * | 3/1998 | Hohlen | 602/18 |
| 5,944,681 A | * | 8/1999 | Hardeman | 602/60 |
| 6,030,354 A | * | 2/2000 | Lakusiewicz | 602/4 |

* cited by examiner

Primary Examiner—Denise M Pothier
(74) Attorney, Agent, or Firm—Ernest Kettelson

(57) ABSTRACT

A contact separation cover for a front and back body brace to separate the braces themselves from contact with the skin of a person wearing such braces. The cover provides a layer of continuously smooth, relatively soft flexible sheet material such as flannelette, over the entire inwardly facing side of the brace. The contact separation cover includes connecting or positioning means whereby it can be secured in place on the brace and removed therefrom for such purposes as cleaning and replacement. A pair of tabs or flaps are provided at each opposite end portion of the contact separation cover to fold over corresponding end portions of the brace. Each pair of tabs or flaps have releasable connecting members, such as tiny hooks and loops, for releasable connection of the tabs or flaps when folded over the respective opposite end portions of the brace.

7 Claims, 13 Drawing Sheets

US 6,524,264 B1

FRONT AND BACK BRACE WITH CONTACT SEPARATION COVER

FIELD OF THE INVENTION

This invention relates to a contact separation cover for body braces for both the front and back of a person's body, to separate the brace itself from contact with the person's skin. It does so in a substantially wrinkle-free way, by providing a continuously smooth flexible sheet surface over that part of the brace that faces inward toward the person's body. The cover is also secured to the brace in such a way that it may be removed for cleaning and replacement if and when necessary. The invention includes the combination of the contact separation cover and the brace itself on which it is removably positioned for use.

BACKGROUND OF THE INVENTION

Prior art body braces for the front and back have not included removable covers that provide a substantially wrinkle-free continuously smooth surface of flexible sheet material over that part of the body brace that faces inward toward the person's skin. Such prior art braces can be worn over a person's clothing, so the clothing itself provides contact separation between the brace and the person's skin. The contact separation cover in accordance with this invention and in combination with the brace itself on which it is removably secured is an improvement over the prior art, since such braces with such contact separation covers can be worn under a person's clothing next to his or her skin.

SUMMARY OF THE INVENTION

The contact separation cover in accordance with this invention comprises a panel of flexible sheet material, such as a fabric material like flannelette, having a continuously smooth surface for placement over the side of the body brace that faces the person's body, fold over upper and lower edge portions to provide upper and lower folds of the cover in which to receive the upper and lower edges of the main central portion of the body brace, with a pair of upper and lower tabs or flaps integrally formed at each opposite end of the cover to fold over the outer ends of the brace which project laterally from each opposite lateral extension of the main central portion of the body brace. The fold over tabs or flaps include releasable connection members, such as cooperative tiny hooks and loops on respective end portions of each pair of such tabs or flaps which releasably inter-connect when brought together. The folded over free ends of the upper and lower edge portions of the cover that provide the folds to receive the upper and lower edges of the main central portion of the brace, include an elastic strip which when in its normally contracted position tightens the grip on the edge of the brace received in such fold to more securely hold the cover in place, and releases such grip when stretched.

DESCRIPTION OF PREFERRED EMBODIMENT

Figure 1:
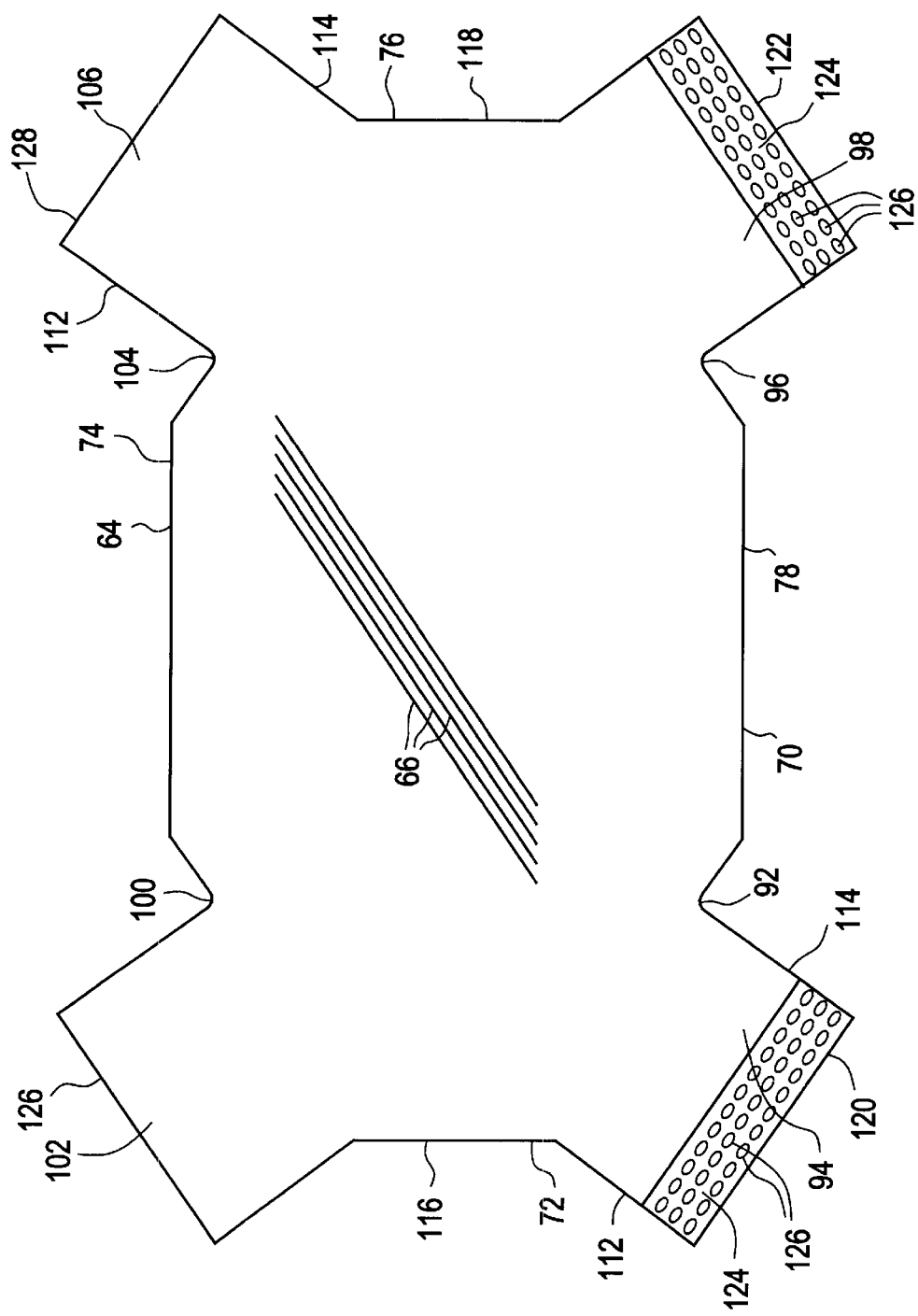
FIG. 1 is a plan view of a sheet of material cut in a configured pattern from which the contact separation cover for a body brace in accordance with this invention is to be made.
Figure 2:
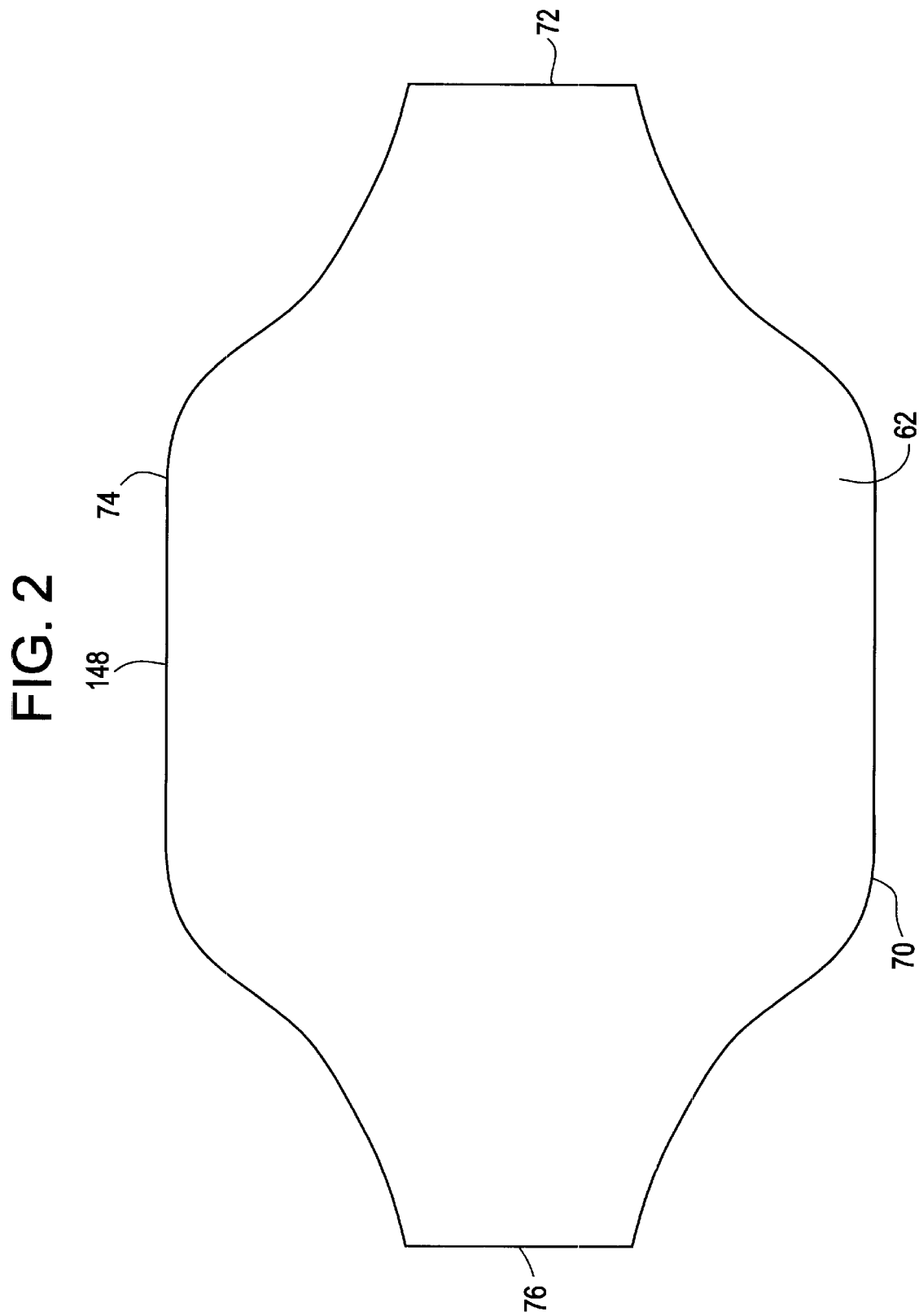
FIG. 2 is a plan view of the back of a contact separation cover for a body brace in accordance with this invention.
Figure 3:
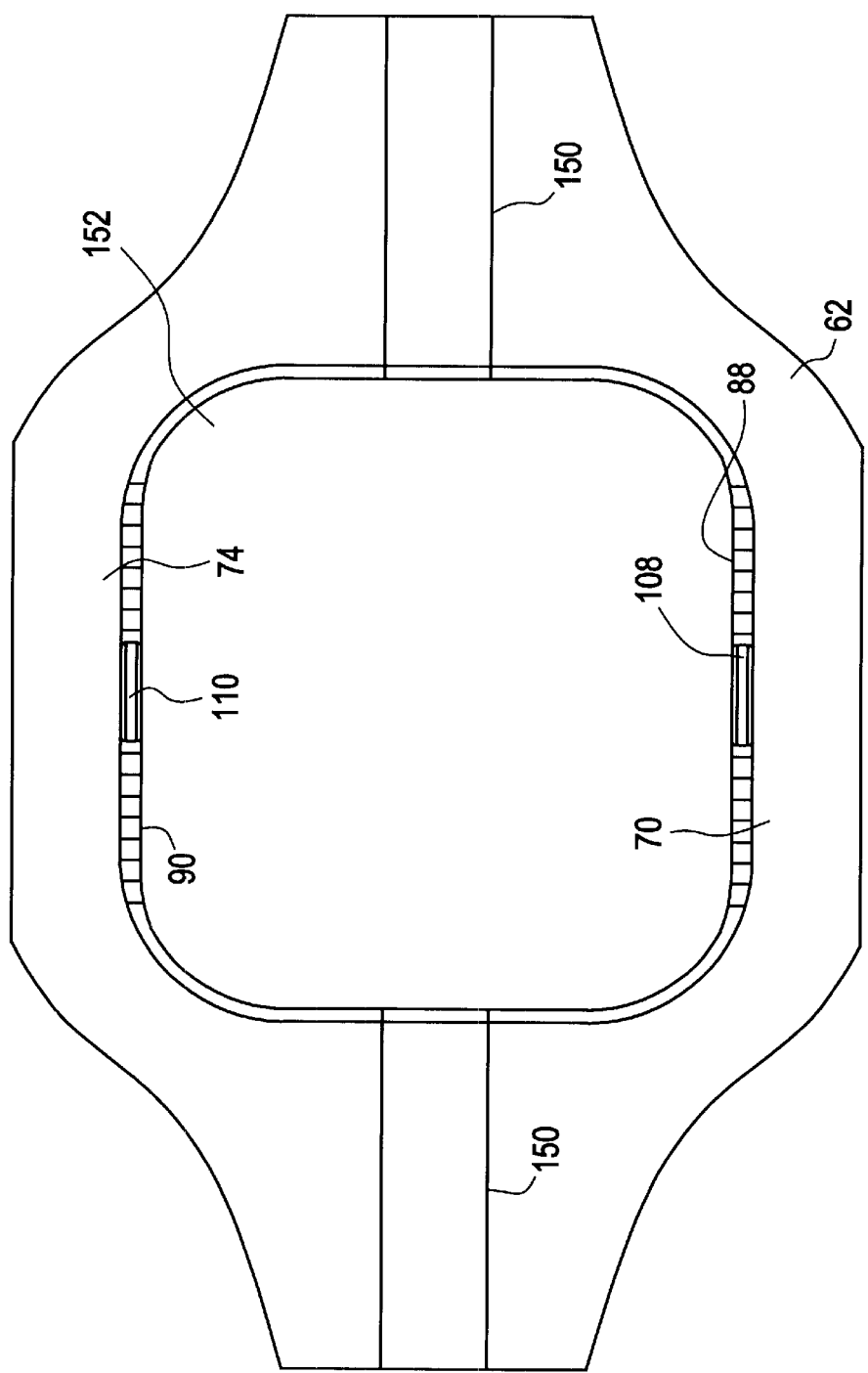
FIG. 3 is a plan view of the front of a contact separation cover for a body brace in accordance with this invention.
Figure 4:
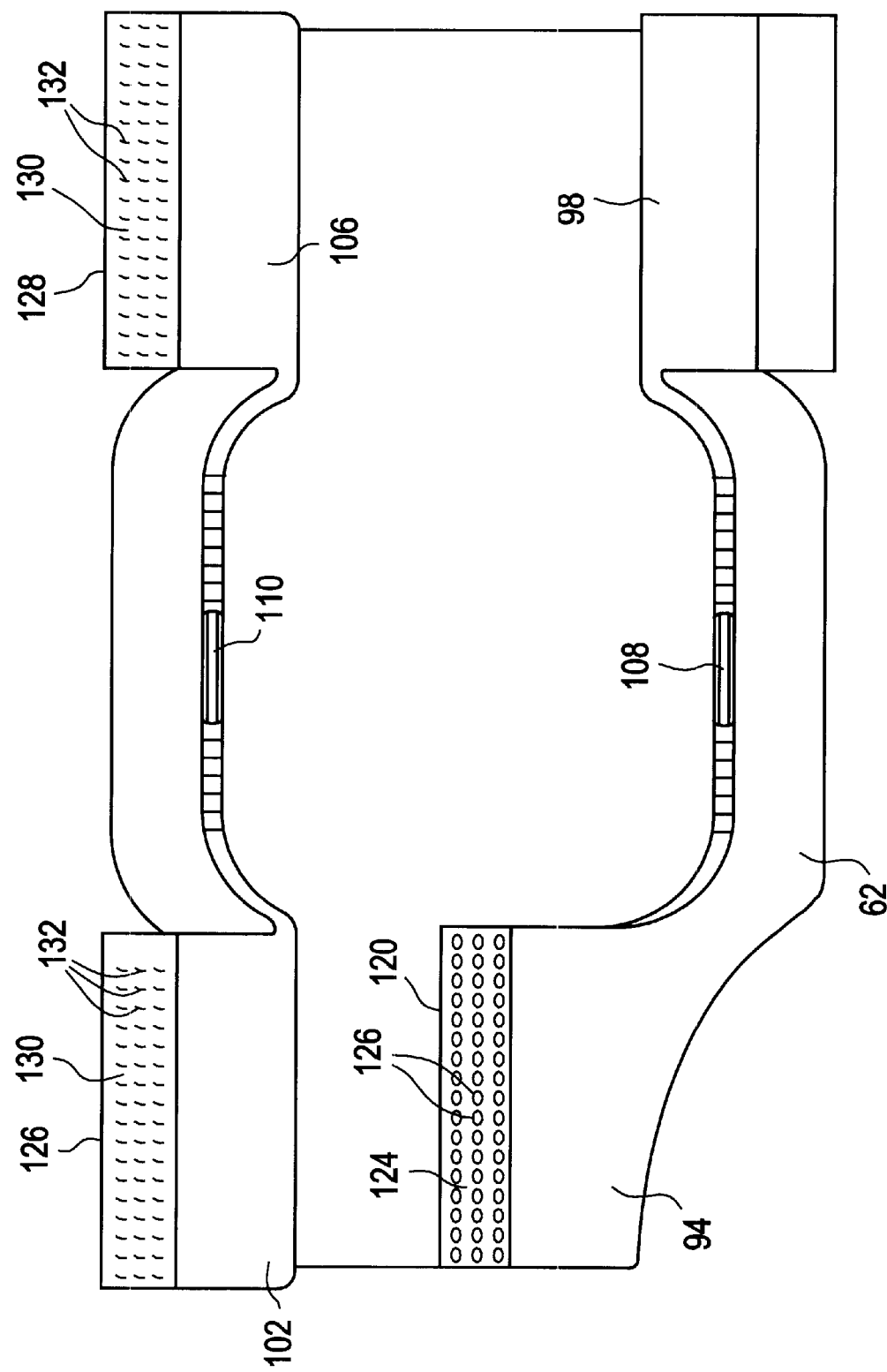
FIG. 4 is a plan view of the front of the contact separation cover seen in FIG. 3 in which each pair of tabs or flaps at each opposite end have been disconnected and folded back to more clearly illustrate their construction.
Figure 5:
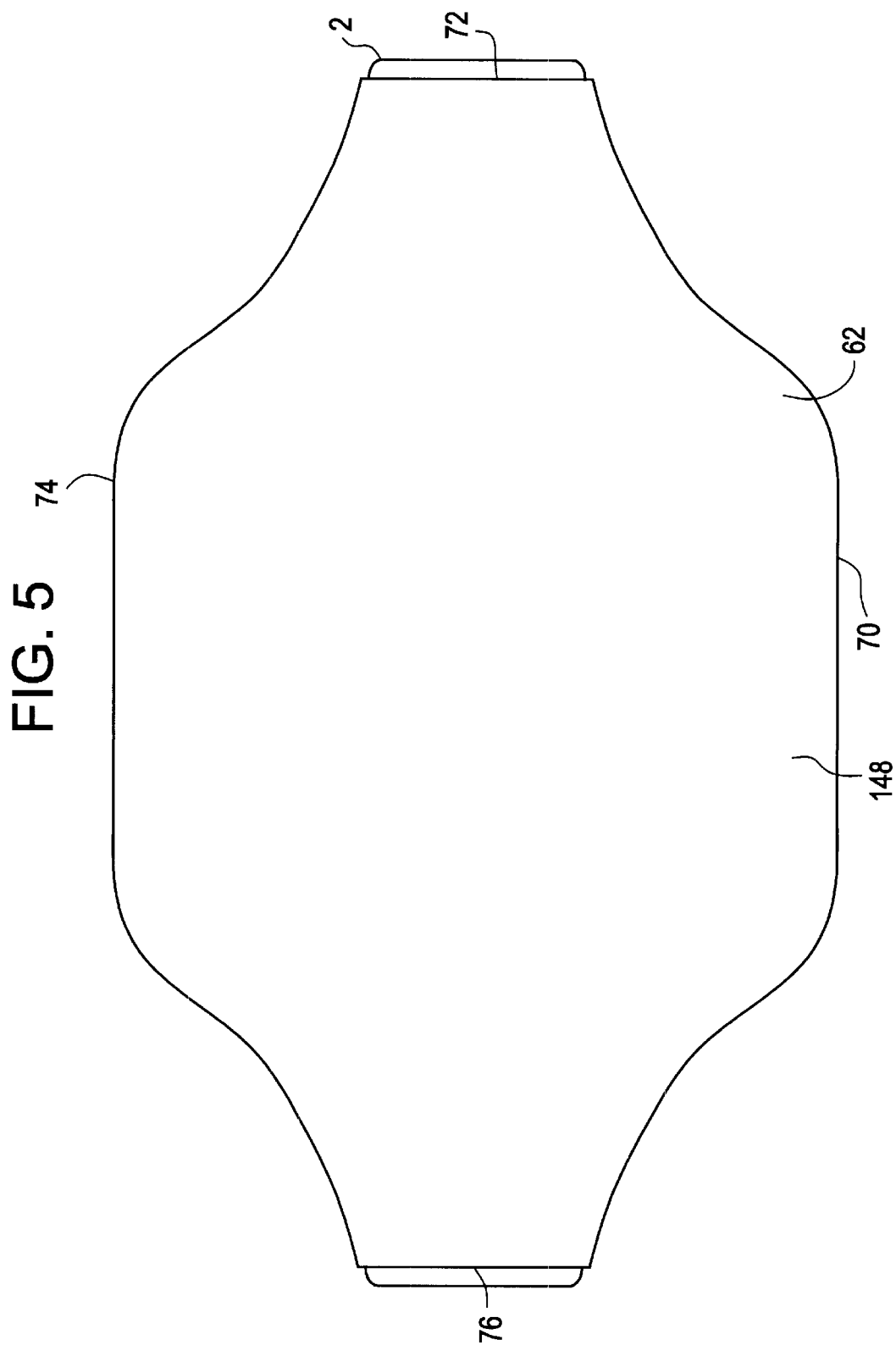
FIG. 5 is a plan view of the back of a contact separation cover for a body brace in accordance with this invention as seen in FIG. 2, but shown covering the body contact or inward facing surface of a body brace on which the contact separation cover has been releasably secured.
Figure 6:
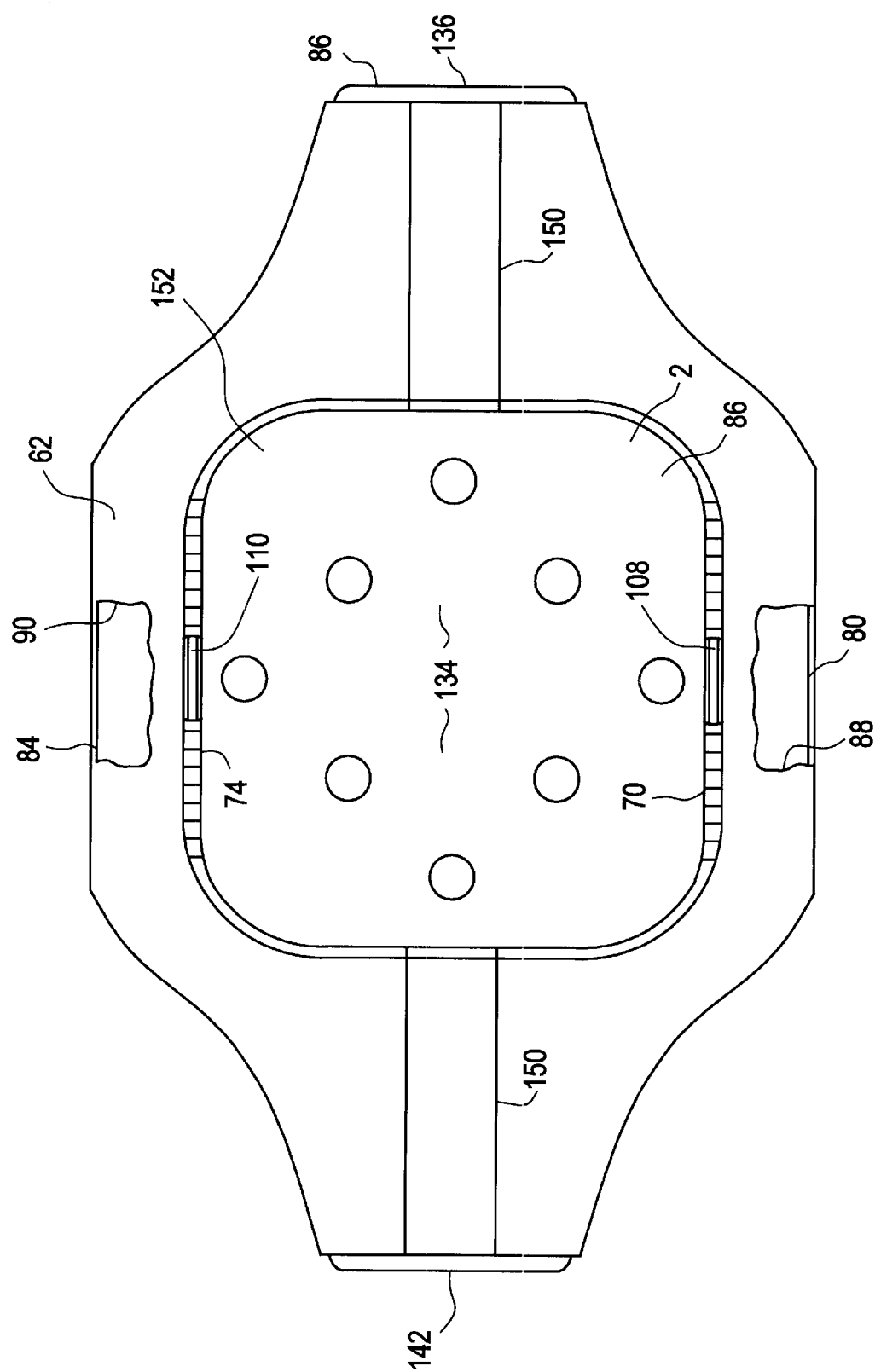
FIG. 6 is a plan view of the front of a contact separation cover for a body brace in accordance with this invention as seen in FIG. 3, but shown in place on a body brace whose outward facing surface is partially in view.
Figure 7:
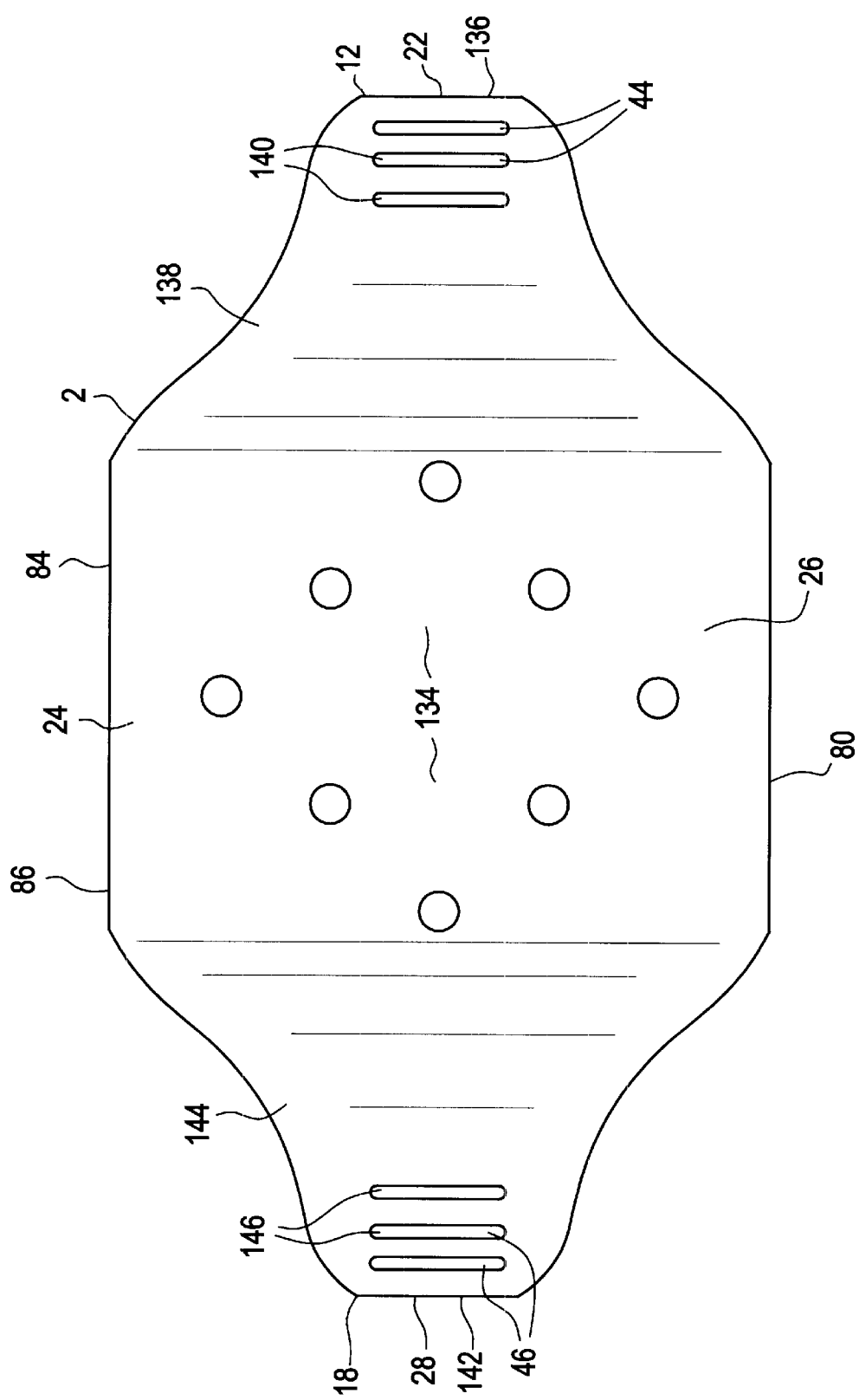
FIG. 7 is an elevation view of the outward facing surface of a front body brace on which the contact separation cover is used in accordance with the combination cover and brace invention disclosed herein.
Figure 8:
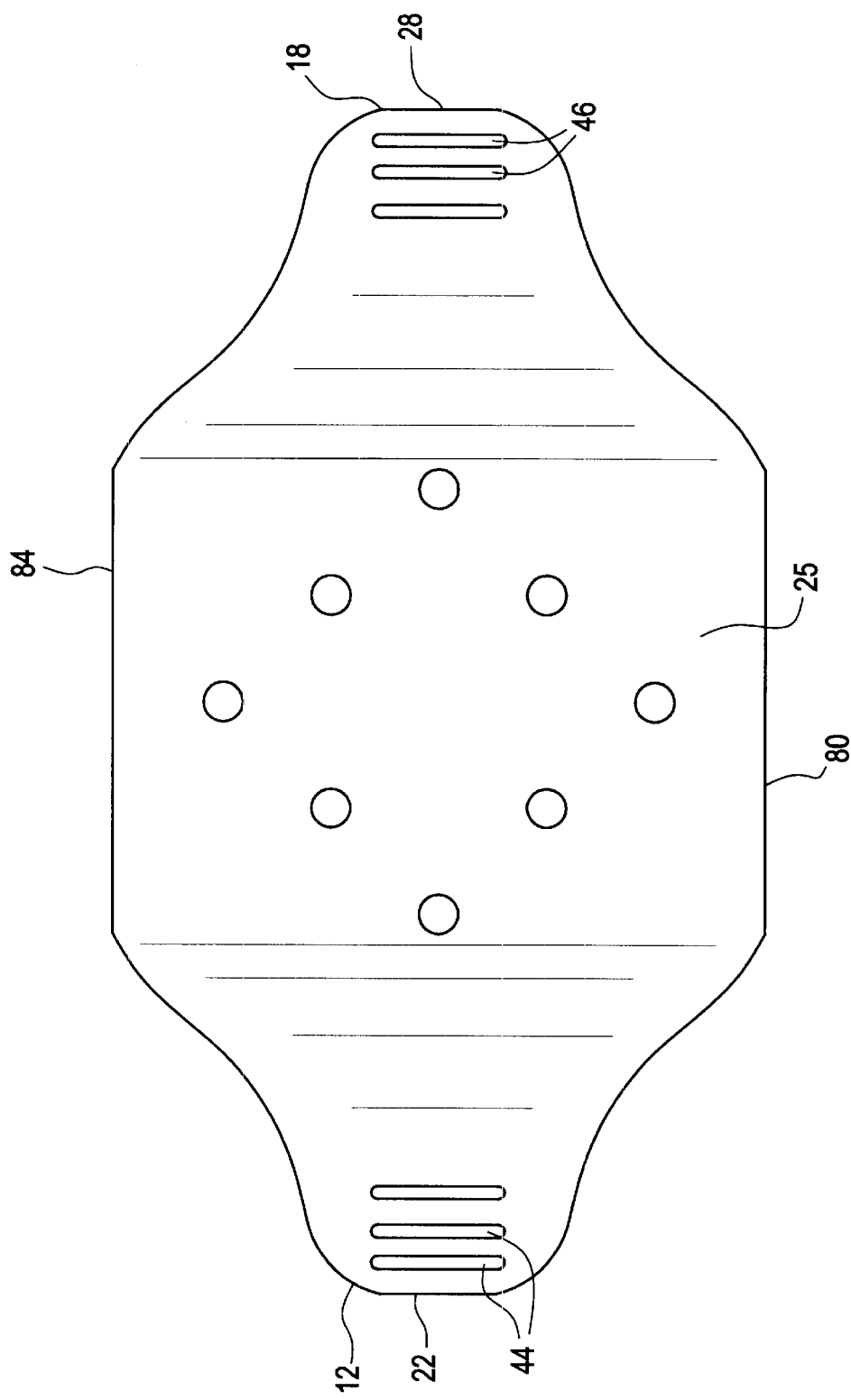
FIG. 8 is an elevation view of the opposite or inward facing surface of a front body brace on which the contact separation cover is used in accordance with the combination cover and brace invention disclosed herein.
Figure 9:
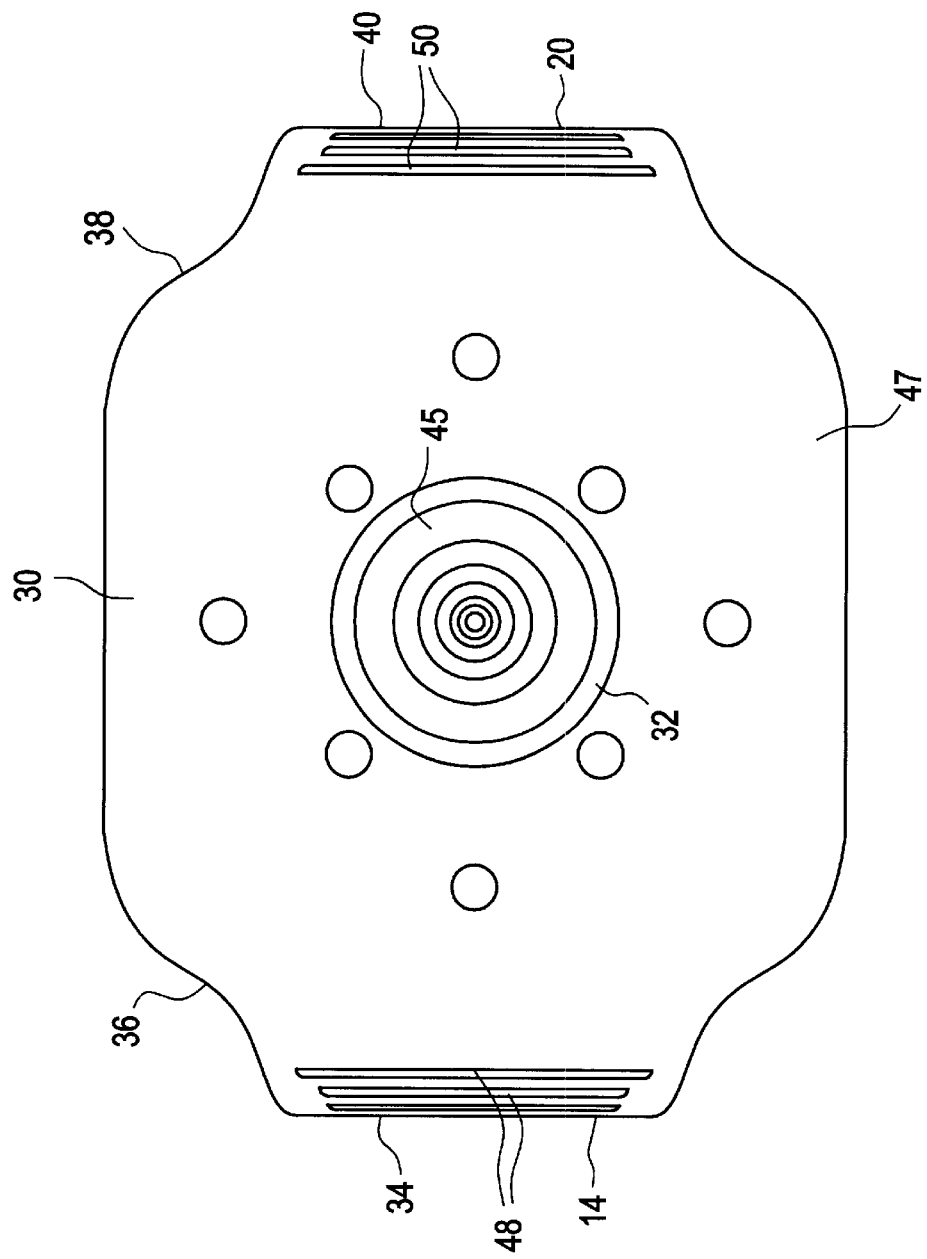
FIG. 9 is an elevation view of the outward facing surface of a back body brace on which the contact separation cover is used in accordance with the combination cover and brace invention disclosed herein.
Figure 10:
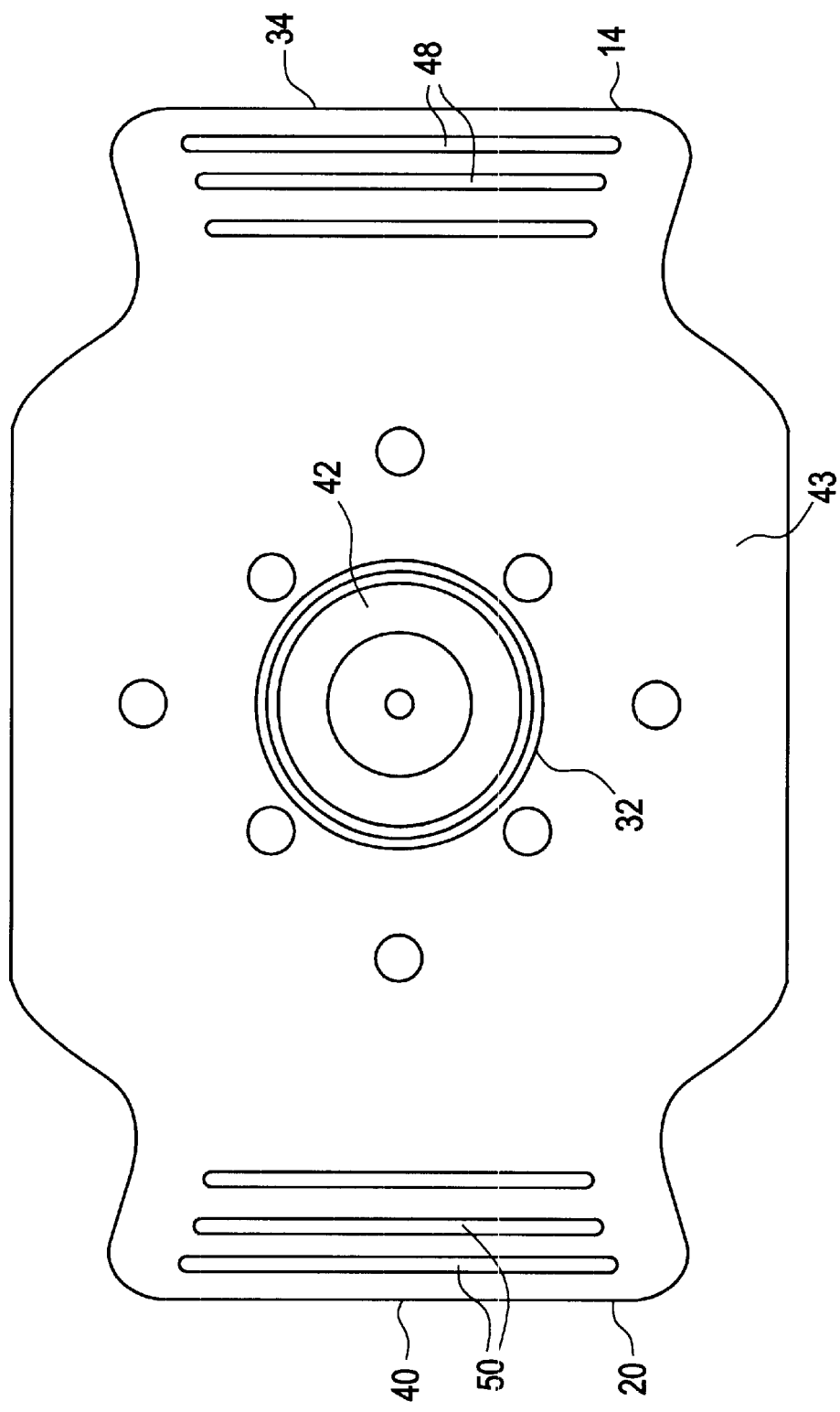
FIG. 10 is an elevation view of the opposite or inward facing surface of a back body brace on which the contact separation cover is used in accordance with the combination cover and brace invention disclosed herein.
Figure 11:
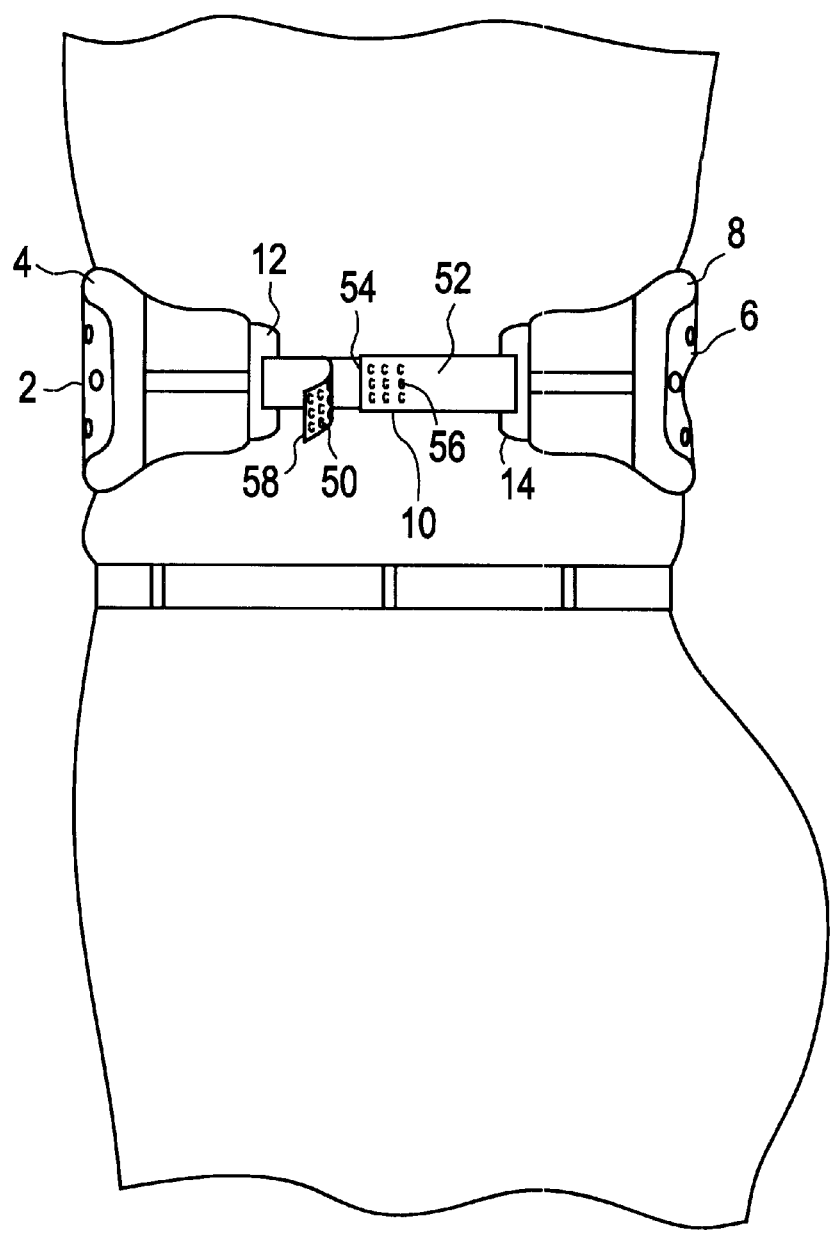
FIG. 11 is an elevation view from one side of a front body brace and back body brace in combination with the contact separation covers on each in accordance with the combination invention disclosed herein, shown secured in place on the front and back mid-portions of a person's body.
Figure 12:
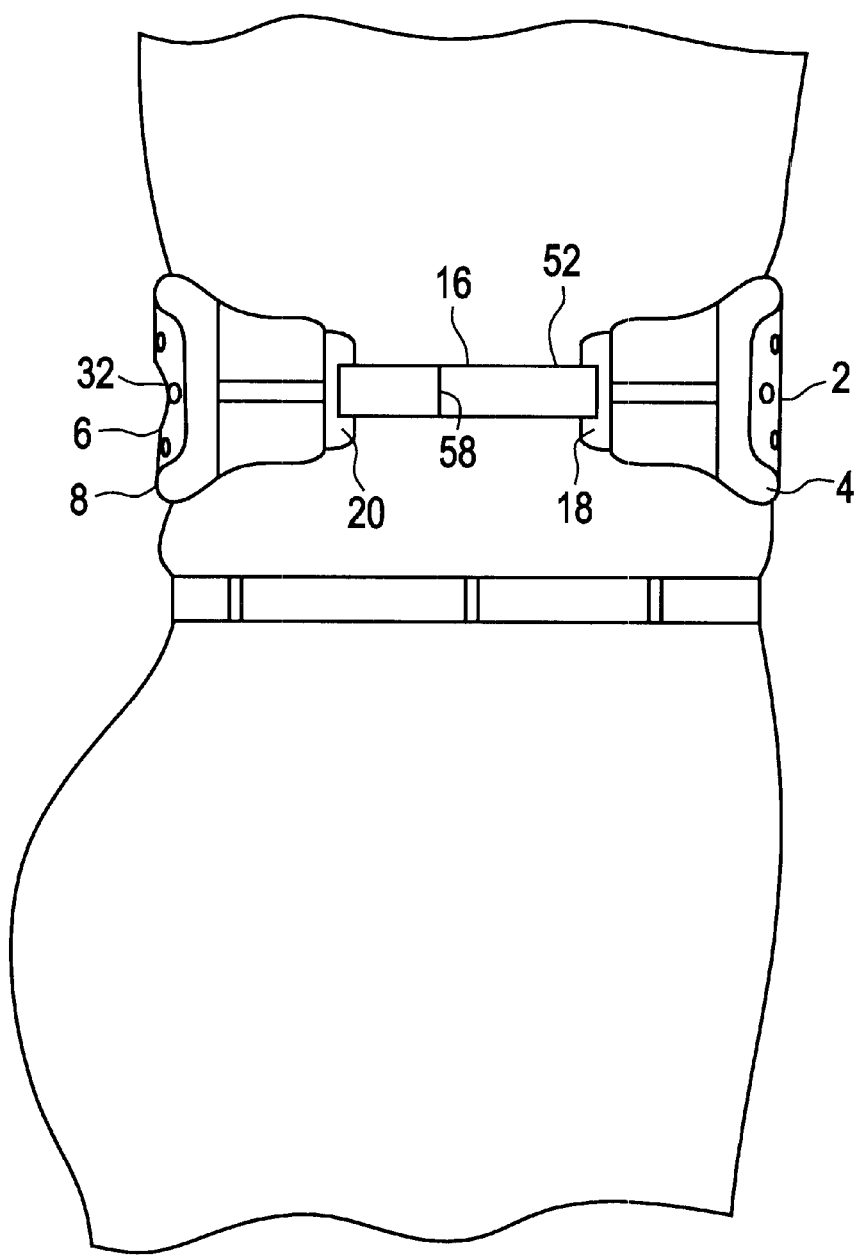
FIG. 12 is an elevation view of the front and back body braces in place on the midportion of a person's body as shown in FIG. 11, but from the other side.
Figure 13:
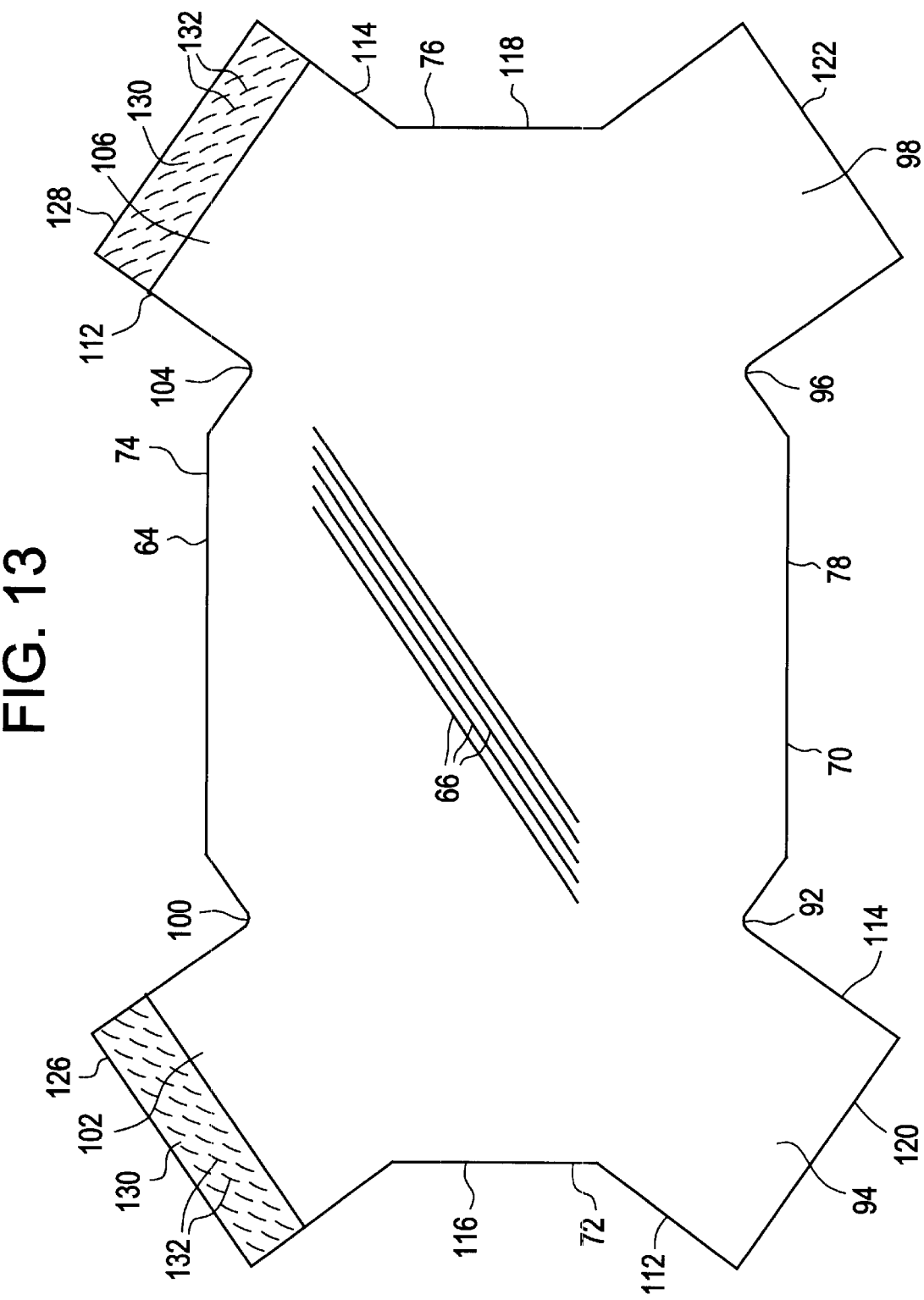
FIG. 13 is a plan view of a sheet of material cut in a configured pattern as shown in FIG. 1, but from the other side.

A front and back brace with a contact separation cover in accordance with this invention, comprises a front brace 2, a contact separation cover 4 for the front brace 2, a back brace 6, a second contact separation cover 8 for the back brace 6, a first flexible strap assembly 10 to connect one side 12 of the front brace 2 to one side 14 of the back brace 6, and a second flexible strap assembly 16 to connect the other side 18 of the front brace 2 to the other side 20 of the back brace 6.

In one embodiment, the front brace 2 comprises a rigid panel of clear plastic material such as polycarbonate, having a first side edge 22, an arcuate wall 24 extending laterally from said first side edge 22 having its convex side 26 facing forwardly away from the front portion of the body of a person wearing said front brace 2. Its concave side 25 faces inwardly toward the person's body. The arcuate wall 24 terminates at a second side edge 28, spaced apart from said first side edge about eleven inches measured on a straight line between them. The back brace 6 in this embodiment also comprises a rigid panel of similar clear plastic material, having a planar wall portion 30 with a spherical segment 32, a first side edge 34 of the back brace 6 from which a first connecting portion 36 extends at a diagonal to the planar wall portion 30 with which the connecting portion 36 is integrally formed, a second connecting portion 38 integrally formed with said planar wall portion 30 extends at a diagonal from the other side thereof to terminate in a second side edge 40 of the back brace 6.

The first side edge 34 of the back brace 6 and the second side edge 40 thereof are spaced apart about eleven inches measured on a straight line between them. The spherical segment 32 is integrally formed in the center of the planar wall portion 30, with its convex side 42 facing forwardly and inwardly from the inward facing surface 43 of the back brace 6 toward the back portion of the body of a person wearing such brace. The concave side 45 of the spherical segment 32 faces rearwardly and outwardly from the outwardly facing surface 47 of the back brace 6, and faces away from the body.

The front brace 2 includes one or more strap receiving slots 44 located inwardly from side edge 22 and one or more strap receiving slots 46 located inwardly from side edge 28. The back brace includes one or more strap receiving slots 48 located inwardly from side edge 34 and one or more strap receiving slots 50 located inwardly from side edge 40. The first flexible strap assembly 10 is received through a slot 44 near side edge 22 of the front brace 2 and extends rearwardly therefrom for reception in one of the slots 48 near side edge 34 of the back brace 6. The second flexible strap assembly 16 is received through a slot 46 near side edge 28 of the front brace 2 and extends rearwardly therefrom for reception in one of the slots 50 near side edge 40 of the back brace 6.

Each strap assembly 10 and 16 comprise an elongated strap 52 of flexible material having one free end 54 on which a panel 56 of tiny flexible hooks are positioned, and an opposite free end 58. The inwardly facing surface 60 of the elongated strap 52 includes a plurality of tiny flexible loops which releasably interconnect with the tiny flexible hooks on panel 56 when brought into contact with each other. The elongated strap 52 extends first in one direction between the respective slots on respective sides of the front brace 2 and back brace 6 and then is doubled back to overlap the respective free ends 54 and 56 which brings the panel 56 having the tiny flexible hooks into facing relationship with the inwardly facing surface 60 of the strap 52 and the tiny flexible loops thereon for releasable interconnection therewith. The more the ends of the elongated strap 52 are overlapped and releasably interconnected as described, the shorter the flexible strap assemblies are between their respective ends of the front brace 2 and the back brace 6. The less they are overlapped and releasably interconnected, the longer. Thus, the strap assemblies 10 and 16 are adjustable to shorten and lengthen the distance between the front brace 2 and the back brace 6, to thereby bring the front brace 2 into snug bearing relationship against the front portion of any wearer's body and the back brace 6 into snug bearing relationship against the back portion of the wearer's body, and to releasably hold them in such position.

Front and back panels of any other construction which are intended for use against the bare skin of the wearer's body may also be used with the contact separation covers 4 and 8 of this invention to separate the panel itself from contact with the skin of the wearer.

The contact separation cover 4 for the front brace 2 and the contact separation cover 8 for the back brace 6 in the embodiment described above may be the same. Therefore, the detail construction of only one particular contact separation cover 62 will be described in this specification, and that particular contact separation cover 62 can be used as both the contact separation cover 4 for the front brace 2 and as the contact separation cover 8 for the back brace 8.

The contact separation cover 62 comprises a configured panel 64 of flexible sheet material, preferably woven such as flannelette, or which otherwise has a texture that includes a plurality of individual but integrally formed strands 66, each of which extends substantially parallel to each of the others to provide a grain in the configured panel 64 of flexible sheet material. The strands 66 are substantially contiguous and have a degree of elasticity that enables some stretching away when pressure is applied in one direction and return to the original position when such pressure is released. When the configured panel 64 is to be cut from an original piece of such flexible sheet material, the pattern for the configured panel 64 is laid cross-wise on the grain of the material whereby the strands 66 extend at a diagonal from the lower edge 70 of the panel 64, starting near one end edge 72 thereof and extending upwardly at such diagonal toward the upper edge 74 thereof near the opposite end edge 76 thereof. The configured panel 64 is then cut from the original piece of material around the configured peripheral edge 78 traced by the pattern when so positioned on that original piece of material. The configured panel 64 when constructed by cutting from the original piece of flexible sheet material in this way has a cross-grain that improves its stretch-ability.

The lower edge 70 and upper edge 74 of the configured panel 64 are spaced apart a distance which is about two inches more than the lower edge 80 and upper edge 84 of the brace member 86 on which it is to be used, which allows for turning over the lower edge 70 on itself about one inch and the upper edge 74 over on itself about one inch to provide a lower receiving pocket 88 and an upper receiving pocket 90 to receive respectively the lower edge 80 and upper edge 84 of the brace member 86.

The lower edge 70 of the configured panel 64 extends in a substantially straight line until it approaches the end edge 72 on one side and the end edge 76 on the other side, whereupon it curves upwardly at each side on a radius that corresponds to the radius at the same location of the lower edge 80 of the brace member 86. The lower edge 70 terminates at one side at the lower connecting edge 92 of an integrally formed first connecting flap 94 and at the opposite side at the lower connecting edge 96 of an integrally formed second connecting flap 98.

The upper edge 74 of the configured panel 64 extends in a substantially straight line until it approaches the end edge 72 on one side and the end edge 76 on the other side, whereupon it curves downwardly at each side on a radius which corresponds to the radius at the same location of the upper edge 84 of the brace member 86. The upper edge 74 terminates at one side at the upper connecting edge 100 of an integrally formed third connecting flap 102 and at the opposite side at the upper connecting edge 104 of an integrally formed fourth connecting flap 106.

A first strip 108 of braided elastic is stretched and then sewn to the configured panel 64 along the lower edge 70. When the elastic strip 108 is then allowed to contract, it gathers the adjacent material of the configured panel 64 causing the lower edge 70 to fold over forming the lower receiving pocket 88. A second strip 110 of braided elastic is stretched and then sewn to the configured panel along the upper edge 74. When the elastic strip 110 is then allowed to contract, it gathers the adjacent material of the configured panel 64 causing the upper edge to fold over forming the upper receiving pocket 90.

The first connecting flap 94 extends at a diagonal downwardly from the lower edge 70 of the configured panel 64 and away therefrom toward one direction. The second connecting flap 98 extends at a diagonal downwardly from the lower edge 70 of the configured panel 64 and away therefrom toward the opposite direction. The third connecting flap 102 extends at a diagonal upwardly from the upper edge 74 of the configured panel 64 and away therefrom toward the same direction as the first connecting flap 94. The fourth connecting flap 106 extends at a diagonal upwardly from the upper edge 74 of the configured panel 64 and away therefrom toward the same direction as the second connecting flap 98. The angle at which each of the four connecting flaps extend is selected which will position their respective side edges 112 and 114 substantially parallel to the respective side edges 116 and 118 of the configured panel 64, after the lower edge 70 and upper edge 74 of the configured panel 64 have been gathered by contraction of the respective elastic strips 108 and 110 as described above, and the first connecting flap 94 is folded upwardly to overlap the third connecting flap 102 as it is folded downwardly, and the second connecting flap 98 is folded upwardly to overlap the fourth connecting flap 106 as it is folded downwardly.

The outer free edge 120 of the first connecting flap 94 and outer free edge 122 of the second connecting flap 98 each include a releasable connection panel 124 having a plurality of tiny flexible loop members 126 thereon. The outer free edge 126 of the third connecting flap 102 and outer free edge 128 of the fourth connecting flap 106 each include a cooperative releasable connection panel 130 having a plurality of tiny flexible hook members 132 thereon. When the respective connecting flaps are folded over as described above, the releasable connection panel 126 of the first connecting flap 94 overlaps and comes into registration with the cooperative releasable connection panel 130 of the third connecting flap 102. When pressed together, the tiny hook members 132 on connection panel 130 releasably interconnect with the tiny loop members 126 on the connection panel 130, to releasably connect the first connecting flap 94 to the third connecting flap 102, and the second connecting flap 98 to the fourth connecting flap 106.

The brace member 86 as described hereinabove includes a relatively broad center section 134 which extends in a slight curve corresponding to the cross-sectional curvature of a human body to terminate at a first end 136 in a relatively less broad first connecting portion 138 having one or more slots 140 to receive one end of the strap assembly 10, and to terminate at its opposite second end 142 in a relatively less broad second connecting portion 144 having one or more slots 146 to receive one end of the strap assembly 16.

The lower edge 80 and upper edge 84 of the brace member 86 as shown and described herein border and curve around the center section 134, then taper downwardly therefrom to border the respective first and second connecting portions 138 and 144, terminating at the respective end edges 136 and 142 of the brace member 86.

The first connecting portion 138 of the brace member 86 is received within the loop formed by the releasable overlapped connection of the first connecting flap 94 and the third connecting flap 102. The second connecting portion 144 of the brace member 86 is received within the loop formed by the releasable overlapped connection of the second connecting flap 98 to the fourth connecting flap 106. One side of the generic contact separation cover 62, as well as of the contact separation covers 4 for the front brace 2 and 8 for the back brace 6, is the body contact side 148 which provides a smooth, continuously unbroken, integral surface of flexible sheet material to bear against the skin of the wearer of the braces. The opposite side of the contact separation covers includes the overlapped connections 150 of the connection flaps as described above, and there is an open space 152 therebetween, the overlapped connections 150 and open space 152 facing outwardly away from body of the person wearing the braces.

The contact separation cover in accordance with this invention is thus secured to the brace member to provide a flexible sheet barrier between the surface of the brace members and the skin of the person wearing the brace members. It will be obvious from the description of the foregoing embodiments of the braces and of the contact separation cover that any number of variations thereof are possible which are still within the scope of this invention, namely a contact separation cover for body braces and the combination of body braces of any kind with a contact separation cover to fit any such brace. The invention does so in a way that provides a smooth, continuously unbroken, integral surface of flexible sheet material to bear against the skin of the wearer of the braces, positioned between the surface of the brace facing the body of the person wearing the brace and the person's skin, to separate the brace itself from any contact with the skin of the person who is wearing the brace. The contact separation cover in accordance with this invention makes it possible to comfortably wear the braces under a person's clothing for extended periods of time, thereby concealing the braces from view.

I claim:

1. A contact separation cover for a body brace and a body brace in combination wherein said body brace includes a first side to face away from the body of a person when worn, a second side to face toward said body of said person when worn, said contact separation cover comprises a panel of flexible sheet material over said second side of said body brace and integrally formed releasable positioning means for positioning and holding said panel of flexible sheet material over said second side and for removal of said panel of flexible sheet material therefrom, wherein said body brace includes a central portion, a first extending portion extending laterally in one direction from said central portion, wherein said panel of flexible sheet material of said contact separation cover includes an upper edge, a lower edge, a first end edge, a second end edge, a first releasable connecting assembly includes a first flap extending outwardly from said first end edge of said panel of flexible sheet material from a location near said upper edge thereof, a second flap extending outwardly from said first edge of said panel of flexible sheet material from a location near said lower edge thereof, said first flap being positioned to overlap said second flap to form a first receiving loop, a first releasable connecting means to releasably connect said first and second flaps together when overlapped, wherein said first extending portion of said body brace is received in said first receiving loop, said first releasable connecting assembly comprising said first and second flaps and said first releasable connecting means, said integrally formed releasable positioning means includes a first folded over portion of said panel of flexible sheet material along a portion of said upper edge thereof, a second folded over portion of said panel of flexible sheet material along a portion of said lower edge thereof, said first folded over portion terminating in an elongated first free edge a short distance below said upper edge of said panel of flexible sheet material, said second folded over portion terminating in an elongated second free edge a short distance above said lower edge of said panel of flexible sheet material, a first stretched strip of elastic material secured to said first free edge while stretched to thereby gather said first free edge in folds when said first stretched strip of elastic material is released to thereby contract, a second stretched strip of elastic material secured to said second freed edge while stretched to thereby gather said second free edge in folds when said second stretched strip of elastic material is released to thereby contract, said first folded over portion of said panel of flexible sheet material forming a first receiving pocket to releasably position and hold an upper edge of said body brace therein when said elastic strip secured to said first free edge is in its contracted position and to release therefrom when said first elastic strip is stretched to thereby lengthen said first free edge sufficiently to enable removal of said upper edge of said body brace therefrom, said second folded over portion of said panel of flexible sheet material forming a second receiving pocket to releasably position and hold a lower edge of said body brace therein when said second free edge is in its contracted position and to release therefrom when said second elastic strip is stretched to thereby lengthen said second free edge sufficiently to enable removal of said lower edge of said body brace therefrom, including said upper edge and said lower edge of said body brace, wherein said body brace includes said upper edge and said lower edge thereof, said upper edge of said body brace being received in said first receiving pocket of said contact separation cover, said lower edge of said body brace being received in said second receiving pocket of said contact separation cover.

2. A contact separation cover for a body brace and a body brace in combination as set forth in claim 1, wherein said panel of flexible sheet material comprises a fabric material.

3. A contact separation cover for a body brace and a body brace in combination as set forth in claim 1, wherein said panel of flexible sheet material is continuously smooth and unbroken.

4. A contact separation cover for a body brace and a body brace in combination as set forth in claim 1, wherein said panel of flexible sheet material includes a piece of material having a grain comprising a plurality of integrally formed strands of material extending substantially parallel to each other.

5. A contact separation cover for a body brace and a body brace in combination as set forth in claim 4, wherein said strands of material are slightly elastic.

6. A contact separation cover for a body brace and a body brace in combination as set forth in claim 5, wherein said strands of said piece of material extend in a diagonal direction from said lower edge of said panel of flexible sheet material toward said upper edge thereof when said panel of flexible sheet material is placed in position over said second side of said body brace.

7. A contact separation cover for a body brace and a body brace in combination as set forth in claim 1, wherein said first releasable connecting means includes a plurality of tiny hook members on one of said first and second flaps, a plurality of tiny interconnecting members on the other one of said first and second flaps positioned to releasably interconnect with said tiny hook members when said first and second flaps are overlapped.

* * * * *